United States Patent [19]

Alt et al.

[11] Patent Number: 5,360,436
[45] Date of Patent: Nov. 1, 1994

[54] CARDIAC PACING RESPONSIVE TO MULTIPLE ACTIVITY TYPES

[75] Inventors: Eckhard Alt, Ottobrunn; Marcus Matula; Edgar Mestre, both of Munich, all of Germany

[73] Assignee: Intermedics, Inc., Angleton, Tex.

[21] Appl. No.: 863,093

[22] Filed: Apr. 3, 1992

[51] Int. Cl.⁵ .......................................... A61N 1/365
[52] U.S. Cl. ..................................................... 607/18
[58] Field of Search ................................... 607/18, 19

[56] References Cited

U.S. PATENT DOCUMENTS

| | | | |
|---|---|---|---|
| 4,771,780 | 9/1988 | Sholder | 128/782 |
| 4,836,218 | 6/1989 | Gay | 128/782 |
| 5,014,704 | 5/1991 | Alt | 128/419 PG |
| 5,179,947 | 1/1993 | Myerson et al. | 128/419 PG |

*Primary Examiner*—William E. Kamm
*Attorney, Agent, or Firm*—O'Connor, Cavanagh,

[57] ABSTRACT

A variable rate implantable pacemaker responsive to patient exercise senses and distinguishes between distinct and different types of physical activity by the patient, and is programmed to respond by generating different response functions to control the pacing rate according to the specific type of physical activity detected. The response functions are algorithms, taken from the behavior of a healthy person with normally functioning cardiovascular system, of heart rates versus an appropriate parameter of a signal produced by a sensor carried by the patient, for the different types of activity requiring different algorithms, in which the parameter value varies in a predetermined way with exercise. The distinction between the different types of physical activity is derived by techniques including calculation of the absolute level of the sensor signal over time, calculation of the standard deviation relative to the mean of the parameter value of the sensor signal over time, performing pattern recognition by spectral analysis of the sensor signal and organizing different physical stress modes by comparing the various templates so observed with templates representing the different types of physical activity of interest, to determine the specific type of activity in which the patient is engaged, for use in controlling pacing rate.

30 Claims, 6 Drawing Sheets

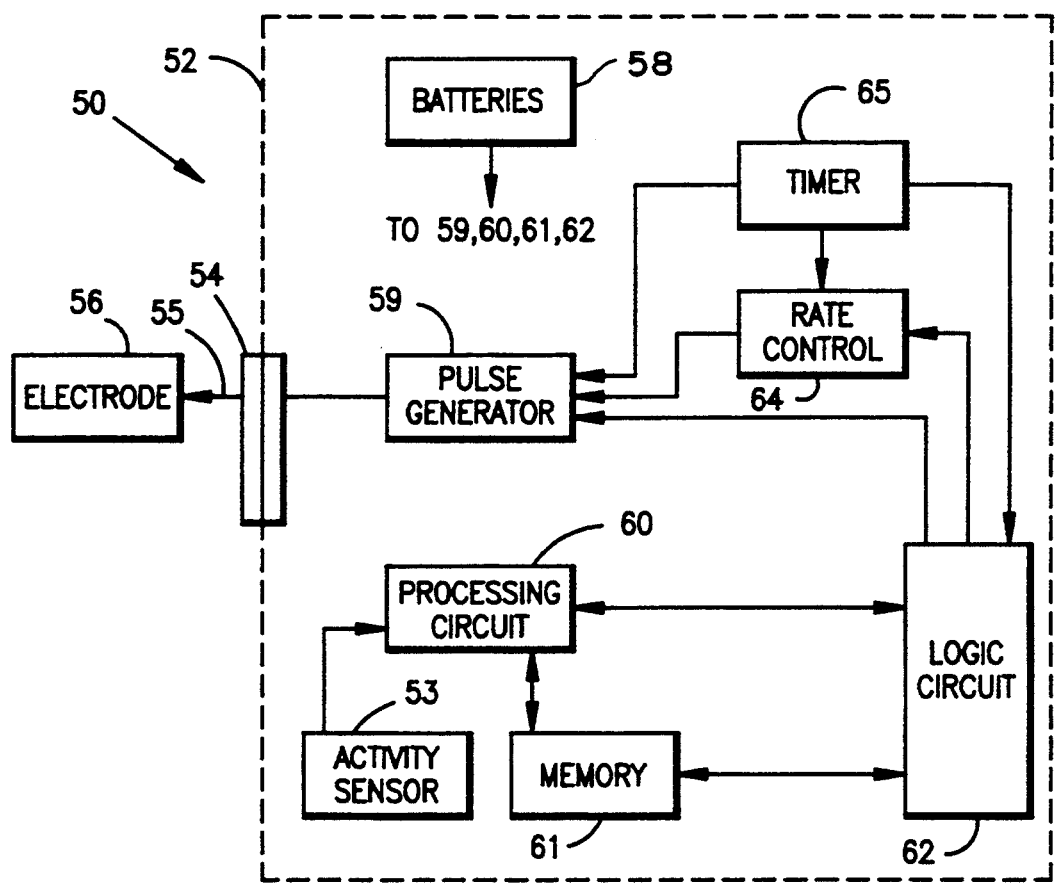
FIG. 6
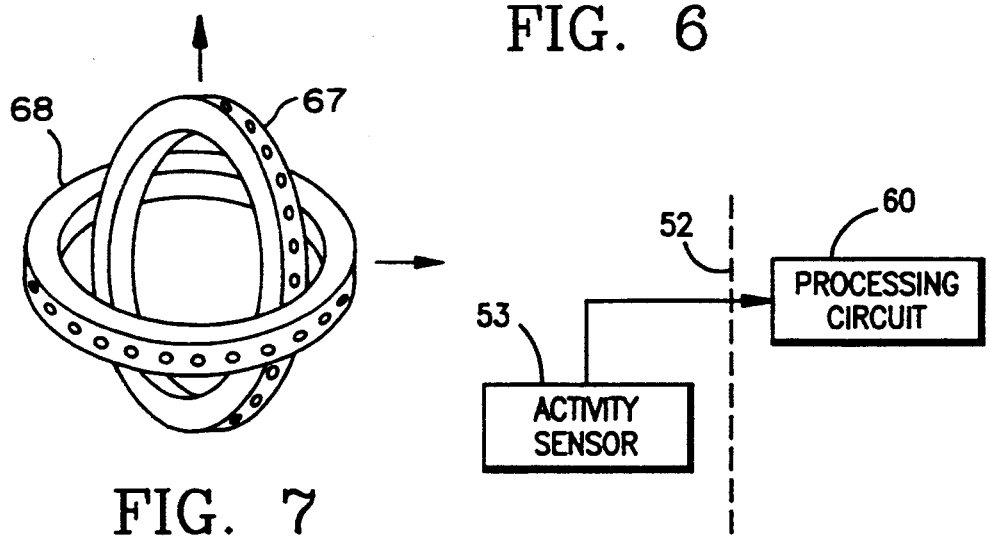
FIG. 7
FIG. 11

CARDIAC PACING RESPONSIVE TO MULTIPLE ACTIVITY TYPES

BACKGROUND OF THE INVENTION

The present invention relates generally to implantable cardiac pacemakers, and more particularly to a pacemaker which is responsive or adaptive to patient exercise, as detected by movement or activity, to generate a pacing rate appropriate to the nature or type of the exercise.

Over the past several years various intrinsic and extrinsic parameters indicative of physical exercise by the pacemaker patient have been suggested for use in controlling pacemaker stimulation rate. The goal is to pace the patient's heart rate in a manner which is adaptive to the current condition of true exercise (or rest) of the patient, corresponding to the intrinsic heart rate of a healthy person with a normal functioning heart when experiencing the same conditions of exercise or rest.

For example, in German Patent No. DE 34 19 439 and related U.S. Pat. No. 4,688,573 (the "'573 patent"), the applicant herein discloses techniques for such rate responsive or rate adaptive pacing using the central venous blood temperature of the patient under various physiological conditions, with separate algorithms defining heart rate as a function of the blood temperature for states of rest and exercise. A decision rule is employed to select which of the algorithms is appropriate at any given time.

Physiological parameters such as blood temperature, blood oxygen saturation, and impedance attributable to respiration (minute ventilation), are exemplary of intrinsic parameters proposed in the past for pacemaker rate control, which, however, are relatively slow to respond to the onset of or changes in the level of exercise by the subject. Therefore, the pacemaker rate variations controlled by detection and use of such parameters tend to some extent to lag the events which make those variations necessary or desirable. Furthermore, detection of these parameters typically requires precision sensors which are expensive to manufacture and involve complex implantation procedures. Hence, although such sensors may quite accurately track the body's varying need for oxygen under differing conditions of rest and exercise for purposes of precise control of the pacing rate, they have not yet achieved great popularity among physicians and patients. Blood oxygen saturation sensing, for example, is considered to be a laboratory curiosity rather than a practical sensing technique for use in controlling pacing rate because of the relative complexity of the sensor apparatus and its implant procedure.

Faster response and less costly and complex manufacturing and implant procedures have been achieved through the use of activity or motion sensors such as accelerometers. It was suggested several years ago to convert mechanical forces, accelerations and pressures into electrical energy and/or signals for use in biomedical technology. One of the earliest techniques proposed in the patent literature was to generate electrical energy from piezoelectric crystals and other mechanoelectrical converters responsive to movement of the individual to power a device implanted in the individual, as disclosed for example in U.S. Pat. Nos. 3,659,615 and 3,456,134. In Journal Biomedizinische Technik 20, pp. 225–228 (1975), Funke described the use of a piezoelectric crystal embedded in silicone rubber and implanted in the pleural space between lung and ribs to detect respiratory rate, for controlling the pacing rate of the patient. U.S. Pat. No. 4,428,380 described using a piezoelectric sensor to measure cardiac activity.

Dahl may have been the first to disclose, in U.S. Pat. No. 4,140,132, the technique of detecting patient activity with a mechanoelectrical converter for the purpose of controlling the rate of a cardiac pacemaker. In Dahl's system, a weighted cantilever arm comprising a piezoelectric crystal was implanted in the patient, the patient's movements caused the cantilever arm to vibrate, the mechanical vibrations were converted to an electrical output signal by the crystal, and the output signal was used as a drive signal for the variable rate pulse generator of the pacemaker. Anderson described a similar system in U.S. Pat. No. 4,428,378 (the "'378 patent"), and used the amplitude of the high frequency content of the converter output signal which was purported to increase with patient movement, as a bandpass signal to control the stimulation rate in an activity-responsive cardiac pacemaker.

Devices such as activity or motion sensors have the distinct advantage that they provide virtually immediate response to patient movements or external forces to generate electrical signals for use in controlling the stimulation pulse rate of the implanted pacemaker. However, they have exhibited serious disadvantages, such as the adverse effect of noise disturbances external to the body, from nearby operating machinery, for example, or emanating from within the body, such as coughing, sneezing, laughing, or the like. Such disturbances are unrelated to physical exercise, but affected the heart rate when early accelerometer-type detectors were utilized for control of the pacemaker stimulation rate. The '378 patent and other prior art sources, such as Proceedings of the European Symposium on Cardiac Pacing, editorial Group, pp. 786 to 790, Madrid, 1985, and Biomedizinische Technik, 4, pp. 79 to 84, 1986, assumed that the maximum acceleration values detected by an activity-controlled cardiac pacemaker in a patient undergoing exercise occur in the range of the resonant frequency of the major body compartments such as the thorax and the abdomen, at approximately 10 Hz (hertz), and that the maximum sensitivity should be in the range above 10 Hz.

In U.S. Pat. No. 4,926,863 (the "'863 patent"), the applicant herein teaches that detection of the accelerometer or activity signal in a frequency range below 10 Hz, indeed below approximately 4 Hz, is actually highly indicative of true physical exercise by the patient. Moreover, restriction of detection signal frequencies to that range discriminates against and avoids undesirable response to disturbances external and internal to the body. As a result, the effect of disturbances unrelated to exercise can be significantly suppressed during use of a mechanoelectrical converter or like transducer to control the pacing rate.

The '863 patent observes that the amplitude maxima of activity-sensed signals arising from exercise such as walking, climbing stairs, running and bicycling occur with rhythmic motion of the body in the low-frequency range. In contrast, sudden spasmodic movements unrelated to true metabolic exercise produce amplitude maxima in the higher-frequency range, above approximately 10 Hz. Accordingly, the effects of the latter movements, as well as noise disturbances, can be excluded by limiting detection to only the low-frequency content.

By using the low frequency band and by establishing different baseline values as ongoing levels of comparison, the activity pacemaker disclosed in the '863 patent provides fast response and reliable pacing at a variable rate adapted to the level of physical exertion of the patient, closely corresponding to the heart rate of a normal healthy person under the same conditions of physical exertion.

In U.S. Pat. No. 5,031,615 (the "'615 patent"), which is a continuation of the '863 patent, the applicant herein discloses an accelerometer and related processing circuitry which are fabricated in hybrid semiconductor integrated circuit form. The accelerometer is designed in that form as a microminiature mechanoelectrical converter or transducer of suitably low power consumption which, as a consequence of its own construction or of use of associated filter circuitry, provides low pass filtering in a frequency band below about 4 Hz.

In U.S. Pat. No. 5,014,703 (the "'703 patent"), which is also a continuation of the '863 patent, the applicant herein discloses an activity pacemaker which detects patient movement, discriminates between detected movements related to true physical exercise and detected movements arising from forces or causes other than exercise by selectively limiting the detected activity signal to appreciable amplitude values in the low frequency range, samples and compares the detected movements related to exercise in successive equal intervals of time to determine whether the exercise is more vigorous or less vigorous than that which occurred during prior time intervals, and adjusts the pacing rate accordingly. Improved sensitivity to changes in workload is obtained by processing the low-pass accelerometer signal in successive intervals of each block of time, as a moving window.

In U.S. Pat. No. 5,031,614 (the "'614 patent"), the applicant herein discloses a simple and reliable technique for obtaining and using the values of both the frequency and the amplitude components of the activity (accelerometer) signal to control the pacing rate. Both components, frequency as well as amplitude, are obtained by examining only the amplitude of the processed activity signal, using the scanning or moving window technique. Comparison of difference values between blocks provides information regarding magnitude of the patient's exercise at any given instant, and frequency of the repetitions being undertaken in that exercise, whether it involves walking, running, bicycling or other activity. The technique has the advantages of fast reaction to changes in exercise and smoothing out inconsistent short term noise. The presence of both amplitude and frequency information regarding the nature of the patient's exercise allows control to be manifested by the smoothed output to more closely track the heart rate of a healthy person with a normal cardiovascular system engaged in similar activity, according to a particular selected characteristic curve or related data.

The '863, '615, '703 and '614 patents are incorporated herein in their entirety by reference.

These advances and refinements have served to make accelerometer-based cardiac pacing a simple and very effective device for tracking the patient's physical activity constituting true exercise and for controlling the pacing rate accordingly. It has been found, however, that a distinct nonlinearity of the accelerometer signals is exhibited, in the sense of differences in the signal, depending on the type of exercise in which the patient is engaged, notwithstanding identical workloads for the different activities. For example, even with both having the same workload, bicycle exercise generates a distinctly smaller accelerometer activity signal than is generated from treadmill (walking/-running) exercise. Use of the prior techniques of accelerometer-based cardiac pacing would lead to a considerably lower pacing rate for the former than for the latter. Yet, the patient's heart rate should be the same or at least closely similar in both instances.

It is a principal object of the present invention to provide apparatus and methods for controlling the stimulation rate of an activity pacemaker according to the specific type of exercise engaged in by the patient, so that the heart rate is adapted to the true workload.

Another significant object of the invention is to provide techniques for detecting and distinguishing between different types of physical exercise of the patient, and, in response, to perform variable cardiac pacing of the patient's heart according to the particular type of physical exercise which is discerned.

SUMMARY OF THE INVENTION

According to the present invention, the activity-sensing, rate-responsive pacemaker is programmed to provide different response rates, based on an algorithm or algorithmic curve representing the desired responses (i.e., heart rates), for different types of physical activity of the patient. In the presently preferred embodiment and method of the invention, each type of activity is represented by a distinct and different curve or portion of a curve of heart rate (or pacing rate) versus acceleration force (or signal) amplitude, with a transition rate between the two (or more) portions. A family of such curves may be made available in the pulse generator externally programmable rate control software of the pacemaker, distinctively representing two or more different types of physical activity, such as bicycling and walking, from which the attending physician may select the optimal curves (algorithms) for the particular patient.

At low rates of detected acceleration vis-a-vis workload, as in the case of bicycling, the pacing rate is adjusted to provide a heart rate appropriate for that activity. In contrast, where the patient is taking exercise in the form of walking or running, with considerably higher rates of detected acceleration for the same workload (compared to bicycling), the pacing rate is adjusted to fit the curve appropriate for that type of physical activity. Thus, the patient experiences the proper heart rate for different types of activity involving the same workload. An accelerometer type sensor may be used which requires neither the complex manufacturing techniques nor the intricate implant procedures typical of physiologic parameter sensors which have heretofore been employed for rate responsive or rate adaptive pacing.

It is therefore another important object of the present invention to provide an implantable activity-type pacemaker which detects different types of activity or exercise and is adapted to respond by generating an appropriate stimulation rate for the workload associated with the particular type of activity, despite differences in sensor signal level for the different types of activity.

The present invention also utilizes calculations of the quotient of the standard deviation and the mean of the signal generated by the activity sensor to determine whether a particular activity signal is consistent with physiology, or is simply a random occurrence. Random occurrences such as a sudden unsustained movement exhibit a high standard deviation, whereas the more constant signals associated with true activity and exercise display a considerably lower variation from the mean or physiologic statistical norm. This technique is useful to differentiate between different types of physical exercise. Furthermore, calculation of the standard deviation relative to the mean of the signal to differentiate distinct types of exercise can be applied to signals derived from changes in intrinsic physiological parameters (such as blood temperature, respiration, etc.) as indicative of exercise, as well as to pure activity signals derived from the output of a sensor of direct movements (activity) of the subject.

This capability to differentiate between different types of activity from an analysis of the output signal of an exercise responsive sensor may also be used to detect and identify the pattern associated with a particular type of exercise, so that it may be compared with a library of such patterns for recognition and appropriate rate response purposes. A certain pattern or template can be identified for each activity form and signal (again, whether associated with pure detection of movement or of change of a physiologic parameter), and on each occasion that the signal falls into that pattern or template a particular cardiac response curve (e.g., a pacing rate determinant) is designated by means of programming of the pacemaker. If the exercise signal analysis exhibits a different pattern, a different response curve is automatically selected, by virtue of the programming.

Therefore, another object of the invention is to provide devices and methods for rapid identification and differentiation (discrimination) between different types of exercise by analysis of the typical characteristics associated with various forms of exercise, by means of calculating the standard deviation relative to the mean of signals derived from a sensor or sensors employed to detect exercise, whether directly from patient movements indicative of activity or from changes in physiologic parameters, and/or by recognizing differences in the characteristic patterns associated with different types of exercise, so as to provide the proper pacing rate response.

The technique of calculating the variance (standard deviation relative to the mean) of an extrinsic or intrinsic physiological parameter is useful not only to differentiate between different types of physical exercise, but additionally to differentiate between noise or spasmodic reactions and true exercise. Therefore, control of the pacing rate to reflect response to true exercise of the patient may be implemented even in the face of sporadic sensing failures such as intermittent electrical contact attributable, for example, to a fracture of the lead, or in the presence of other noise components on the output signal of the sensor. According to yet another aspect of the invention, then, apparatus and a method are provided for discriminating true and consistent physiological signals such as a patient's sinus rhythm having a variable value depending on patient exercise, from inconsistent or noise signals such as intermittent or otherwise faulty sensing or other noise, to control the pacing rate of a variable rate pacemaker carried by the patient in response to the variable value of the physiological signals.

To that end, a physiological parameter having a variable value representing the extent of exercise engaged in by the patient is sensed and converted to an output signal indicative of substantially the instantaneous value of the parameter and possibly also containing noise components. The output signal is processed by calculating the variance, as the standard deviation, relative to the mean of the output signal over time to discriminate the true variations of the value of the physiological parameter from noise components of the output signal. This calculation includes deriving the quotient of the mean and the standard deviation. The pacing rate of the pacemaker is then controlled in response to the processed output signal to vary the pacing rate according to true variations of the value of the physiological parameter while suppressing any contribution attributable to noise components, and thereby, according to true patient exercise.

Hence, yet another object of the invention is to provide apparatus and methods for discriminating true exercise sensing signals from noise by calculating the standard deviation relative to the mean of the sensing signals, so that any noise components on the signals may be suppressed, to provide the proper pacing rate response.

BRIEF DESCRIPTION OF THE DRAWINGS

The above and other objects, aspects, features and attendant advantages of the present invention will become apparent from a consideration of the ensuing detailed description of presently preferred embodiments and methods thereof, taken in conjunction with the accompanying drawings, in which:

FIG. 6 is a block diagram of a rate responsive pacemaker which may use the multi-activity sensing and response functions of the invention;

FIG. 7 is a perspective view of a pair of mercury ball sensors having a fixed orthogonal orientation, for use in activity sensing in conjunction with the pacemaker of FIG. 6;

FIG. 11 is a partial block diagram illustrating an alternative location of the activity sensor relative to that of the embodiment of FIG. 6.

DESCRIPTION OF PREFERRED EMBODIMENTS AND METHODS

Differences in the amplitude of forces or vibrations detected by an activity sensor (e.g., an accelerometer) for different types of physical exercise are partially attributable to the physical location of the sensor on the person. For example, an accelerometer worn on or implanted in the chest region of the body has greater sensitivity to movements of the upper body than of the legs. When the wearer (i.e., the subject, whether the sensor is carried externally or implanted) of the accelerometer in that location is riding a bicycle, the output signal attributable to that exercise is of much smaller amplitude than that of the signal produced when the wearer is walking or running (e.g., on a treadmill), even though both types of exercise may involve the same or substantially similar workload during any given period.

The heart rate of a healthy person with a normal cardiovascular system would be substantially the same for the same workload regardless of the type of exercise. However, the pacemaker patient whose heart rate is stimulated according to the amplitude of the signal from an activity sensor experiences vastly different pacing rates despite the identical workloads. This non-linearity between activity signal and different type but same workload exercise (bicycling and treadmill merely being examples of different types with which this may occur) must be recognized and compensated for if the patient's heart rate is to be artificially paced in a manner simulating that of the natural pacemaker of a healthy individual.

Figures 1A, 1B:
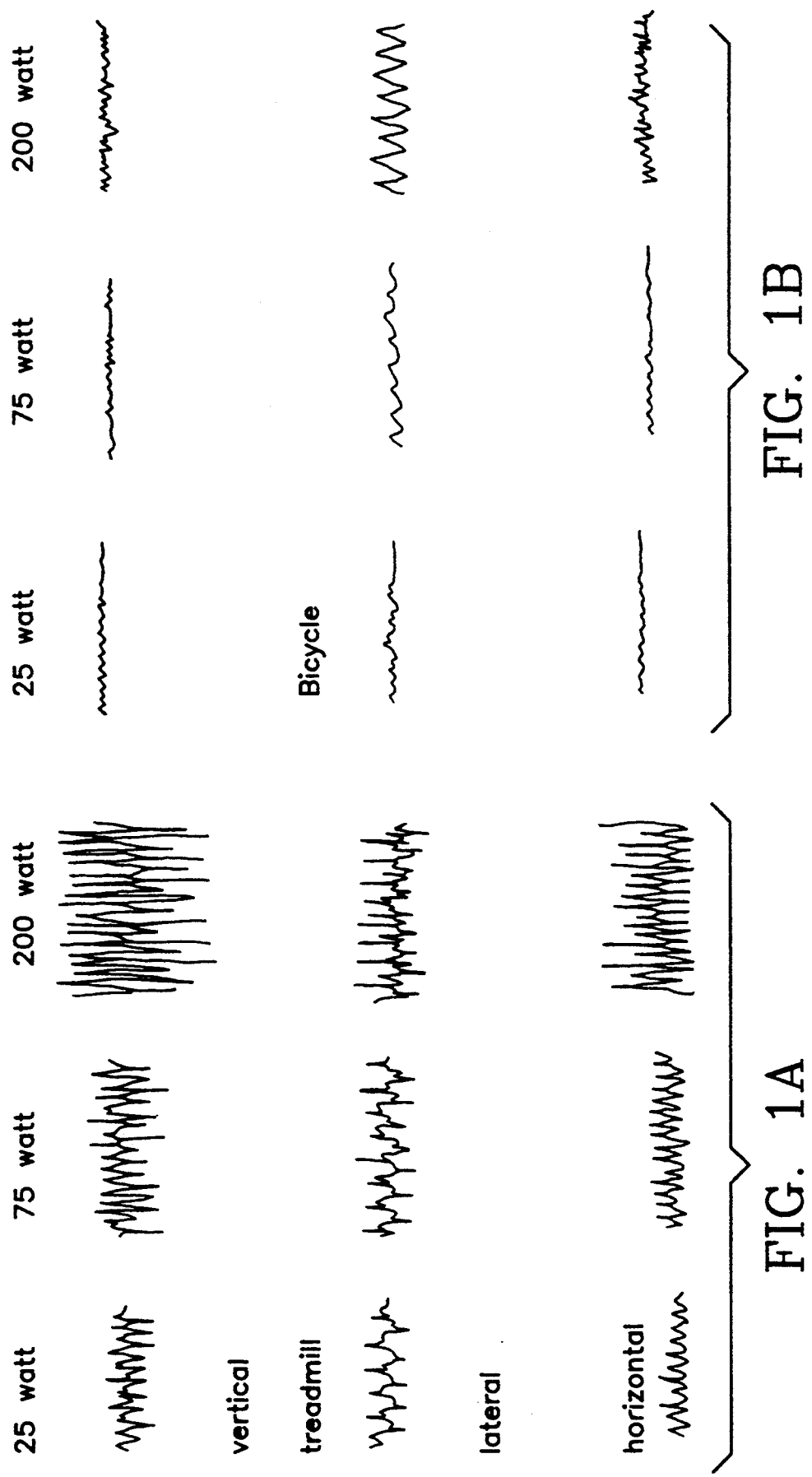
FIG. 1A illustrates several activity or acceleration signals with increasing workloads for treadmill (walking/running) exercise.
FIG. 1B illustrates the same for bicycle exercise.

FIGS. 1A and 1B are based on charts of activity signals arising from forces applied in the vertical, lateral and horizontal directions on an accelerometer worn in the chest area by a healthy volunteer subject during treadmill exercise and bicycle exercise, respectively, with 25, 75, and 200 watts of energy expended. The same units of amplitude are charted on the Y-axis in each case. The activity signals for bicycle exercise are of considerably smaller amplitude than for treadmill activity, regardless of the direction of the accelerational forces. The closest comparison between these two different types of exercise for the same workload is observed for the lateral forces, although the amplitude of the bicycle signal remains much smaller than that of the treadmill signal for each of the three workloads. It is further observed that the bicycle signal for lateral forces is greater than that for vertical forces, for each workload, whereas the reverse is true for the treadmill signal.

These observations might lead one to a simple algorithm or decision rule, namely, if the activity signal amplitude is greater in the lateral direction than in the vertical direction (determined using two differently oriented sensors and a signal comparator), the bicycle curve of pacing rate versus activity signal amplitude is to be used to effect rate control; and if the reverse occurs, i.e., a greater vertical than lateral activity signal amplitude, the treadmill curve is to be used. For such purposes, two distinct and different curves of heart rate versus activity signal amplitude are developed from a healthy subject engaged in the two different types of exercise, and the selection of the appropriate curve is based on that algorithm.

Figure 2A:
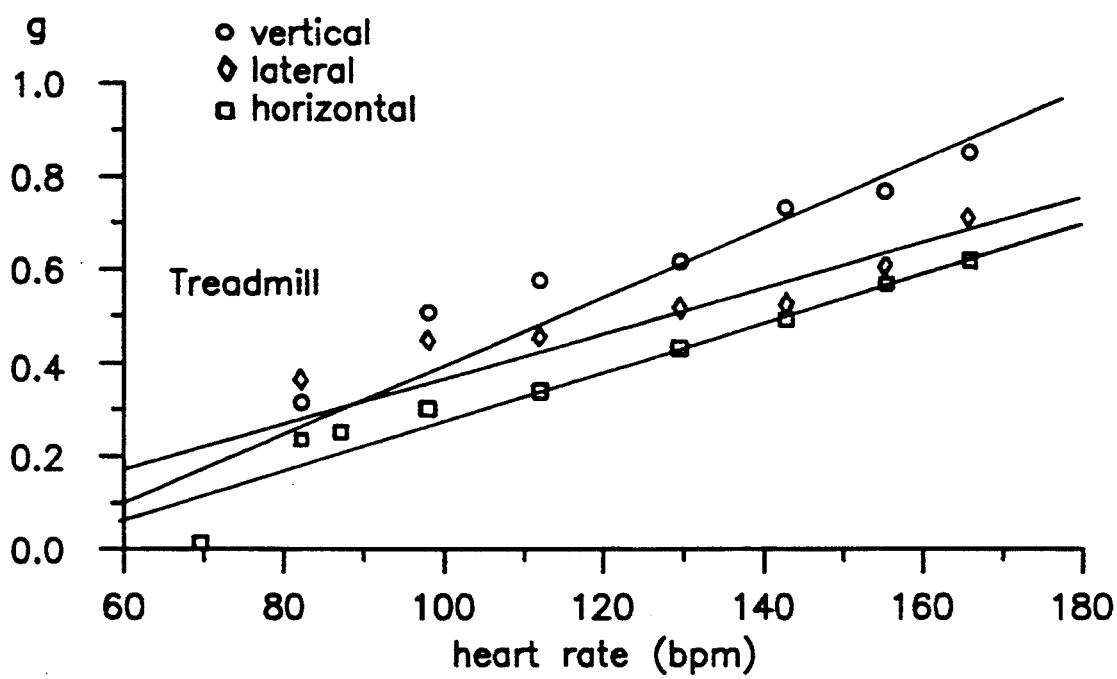
FIGS. 2A and 2B illustrate the relationship between intrinsic heart rate and low pass (frequency band) acceleration signals for treadmill and bicycling, respectively, with increasing exercise and for different sensor orientations.
Figure 2B:
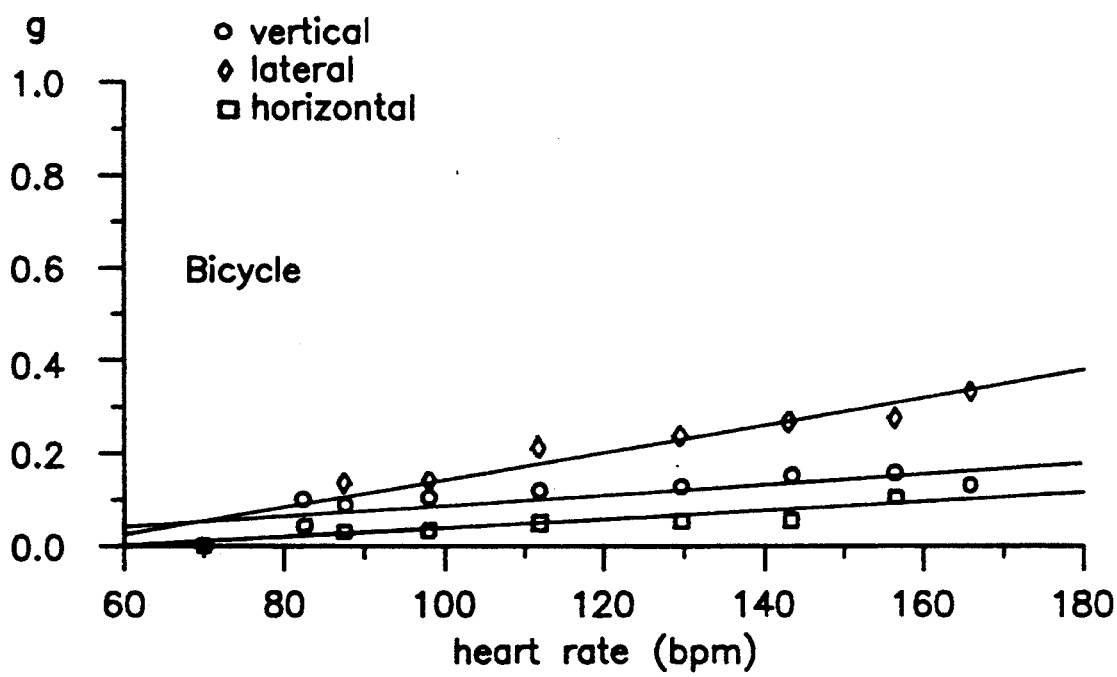

FIGS. 2A and 2B are "curves" of the relationship between the intrinsic heart rate (plotted on the X-axis, in beats per minute (bpm)) and the low pass (e.g., below about 4 Hz) acceleration signals (plotted on the Y-axis, in gravitational units g) obtained from a healthy volunteer subject wearing chest region located, directionally oriented accelerometers during treadmill walking (FIG. 2A) and bicycling (FIG. 2B), for increasing workloads of exercise from 0 to 200 watts. Zero g indicates an absence of accelerational force and work-load. The illustrated slopes are for the vertical, lateral and horizontal directions of accelerational forces on the subject. Each "curve" is a straight line drawn approximately along the mean of the respective plotted points. There is a certain linearity with a high correlation coefficient for all three axes of the activity signal amplitudes corresponding to the three different directions of accelerational force.

FIGS. 2A and 2B illustrate that the slope of each walking curve is steeper (when plotted in this manner) than the slope of the related bicycling curve, which is a consequence of the greater accelerational forces experienced in walking than in bicycling, for the identical workload. For example, an acceleration signal arising from a force in the vertical direction of 0.8 g during walking exercise produces a heart rate of about 150 bpm, whereas for bicycle exercise an acceleration signal consistent with a force of only about 0.1 g in the same direction produces approximately that same heart rate, for this subject.

According to the invention, the proper pacing rate is generated for pacemaker patients regardless of the type of physical exercise engaged in and the nonlinearity of activity signal amplitude versus workload for the different types, by use of an activity pacemaker with different selective response rates. For example, the pacemaker delivers pacing rates for low acceleration activity different from the pacing rates it delivers for higher acceleration activity. Where the patient may engage in a plurality of different types of activity which have substantially different response curves, such as those of FIGS. 2A and B for treadmill and bicycle exercise, as will be true in a large number of cases, two different response rates (e.g., algorithms) are programmed into the pacemaker.

In a preferred embodiment of the invention, only one curve is employed which has a transition from a bicycle range with pacing rates lower than the ideal, to a treadmill range with pacing rates artificially commencing at a value higher than the highest bicycle rate. In an alternative embodiment, the activity pacemaker uses two different algorithmic curves separated by a transition region. In either embodiment, when the detected acceleration force is low, and when this low acceleration is sustained over a critical period of time to be discriminated against random occurrence of low acceleration noise, or other means to be described presently herein are applied to process the signal and rule out random noise and fluctuations, the pacing rate follows the bicycle curve, and at a programmed transition rate, the pacing rate shifts to the treadmill curve. The attending physician may select the most appropriate model or fit for a particular patient from among a family of such curves developed for the pacemaker.

Figure 3:
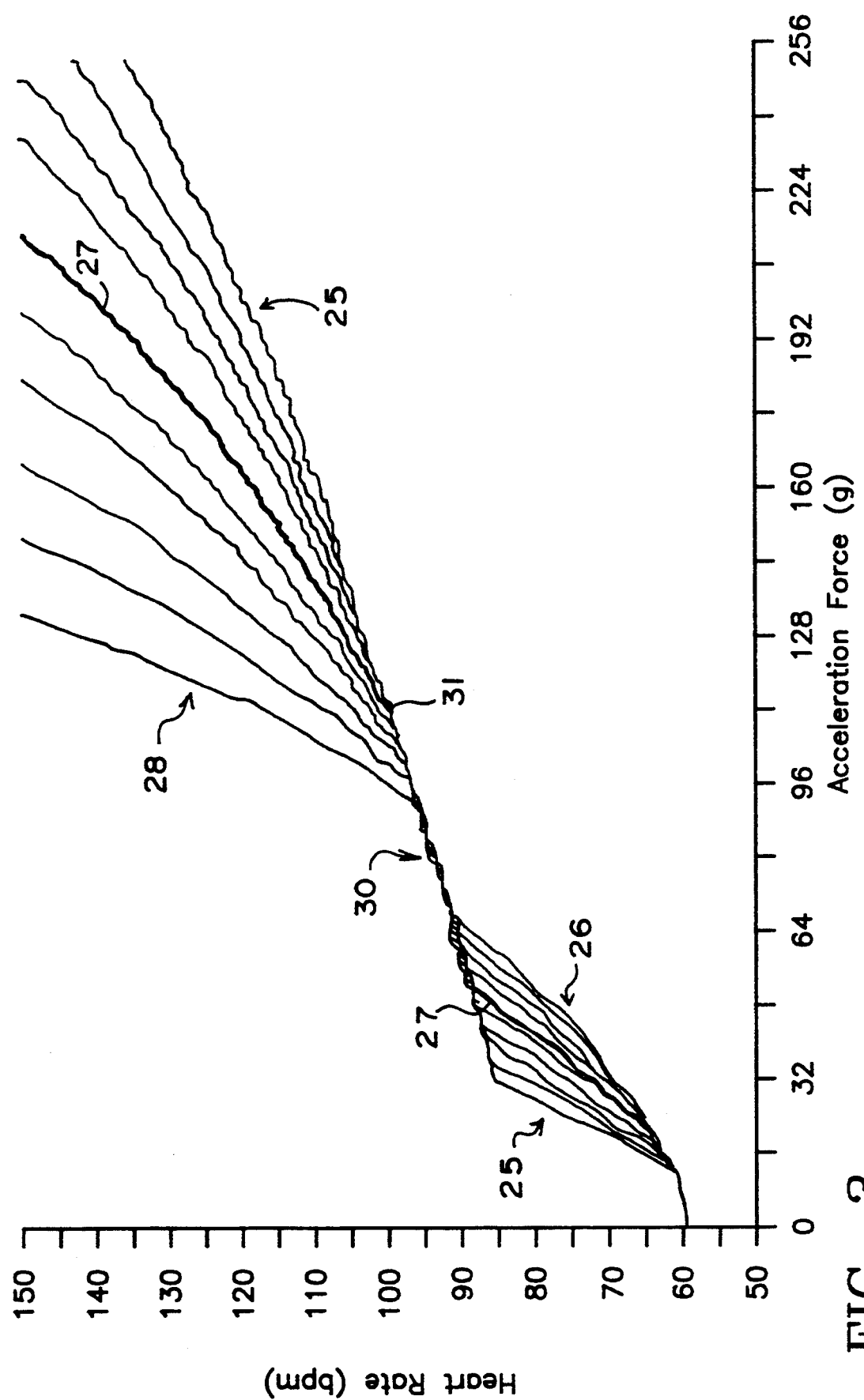
FIG. 3 is an algorithmic curve of pacing rate versus acceleration forces for two different types of activity, for use in one embodiment of a multi-activity pacemaker according to the invention.

An exemplary algorithmic curve for the preferred embodiment or method is shown in FIG. 3, where the X and Y axes are reversed from what was depicted in FIGS. 2A and 2B, i.e., the forces of acceleration detected by the accelerometer are plotted in g's on the X-axis and the heart rate or pacing rate is plotted in bpm or ppm (pulses per minute) on the Y-axis. Consequently, the relative steepness of the slopes is also reversed, with the steeper slope associated with bicycling (more rapid increase in heart rate for smaller increase in acceleration), compared with walking. Although FIG. 3 illustrates a family of curves 25, in practice the attending cardiologist may select a single curve, such as 27, considered to be optimal for the particular patient. The numbers from 0 to 256 along the X-axis are actually digital values rather than g units, corresponding to the range of accelerational forces which may act in a particular direction on the accelerometer at any given period of time. Analog representations of such force in g's could have been used instead. In the range from 0 to about 12 on the X-axis, the pacing rate is calibrated to 60 ppm so that the pacemaker maintains the resting rate at noise levels in that range attributable to random movement of the patient while sitting, for example. At moderate levels of physical activity, in the force range from about 12 to about 48 digital units, the pacing rate along a portion 26 of the curve 27 rises rapidly from 60 to about 88 ppm to reflect rates appropriate to bicycling activity.

At that point on curve 27 (and at similar points on the other curves in the family of curves 25), there is a zone 30 constituting a relatively flat transition interval in which a substantial increase in acceleration force, from about 48 to about 112 units for curve 27, produces only a relatively small increase in pacing rate, from 88 to 98 ppm in this example. The transition zone 30 terminates on the high end in a portion 28 of the curve 27 representing pacing rate versus acceleration force for walking activity. That portion of the curve has a slope which is considerably steeper than the transition zone 30, but less steep than the slope of the bicycling activity portion 26 of the curve, so that the higher acceleration forces (pedal impacts, here) accompanying walking may fairly quickly increase the pacing rate to the maximum of 150 bpm (for this set of curves).

For an activity pacemaker which incorporates the algorithm represented by a curve of FIG. 3, when the patient gets up and commences walking, the paced heart rate jumps immediately to a higher level, past the "bicycling" activity portion 26 of the curve and the transition zone, to the point 31 designated by the lower end of the "walking" activity portion 28. This is the break point between the transition zone and the walking activity portion of the curve. If the patient continues walking with greater accelerational forces, the pacing rate continues to increase as the workload increases, at a rate determined by the "walking" activity portion 28 of the curve. It should be observed that the moderate activity levels represented by bicycling portion 26 of the curve are not encountered during normal walking. The pacing rate will jump immediately to the rate at the lower end of portion 28 of the curve (break point 31), since even the slightest walking activity exceeds the bicycle exercise values, on average.

If the patient commences bicycling activity, the acceleration forces will begin in the lower portion of the 16 to 64 force range and thereafter increase with increasing workload, and the pacing rate will follow that portion of the curve.

Figure 4:
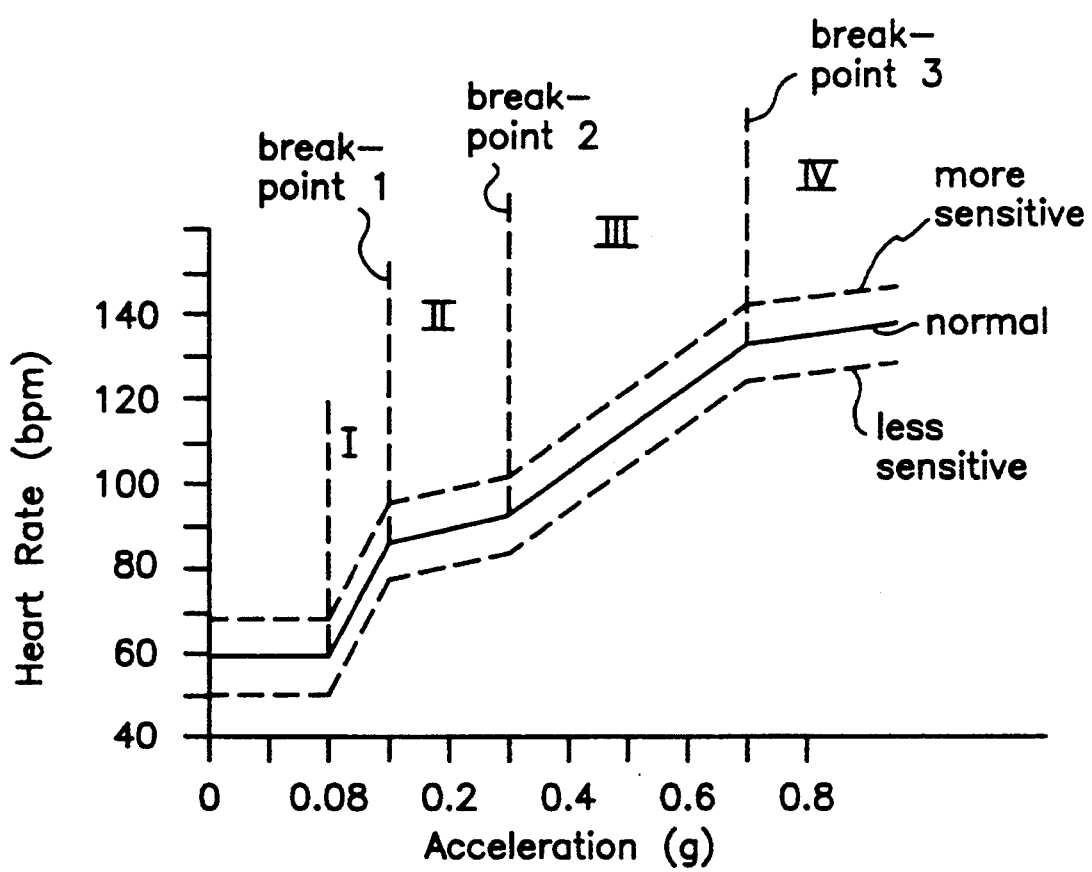
FIG. 4 is an exemplary multiple response curve (algorithm) reflecting the relationship of heart rate and acceleration, for alternative use in multi-activity pacing.

FIG. 4 illustrates a somewhat different multiple activity rate response curve of the relationship between heart rate and acceleration, which may be used in place of that of FIG. 3. The first triggering threshold is set at 0.08 g of acceleration in this example, consistent with the commencement of acceleration forces experienced with bicycle exercise by the patient. This initial triggering increases the patient's heart rate (in region I of the curve) from 60 at the first triggering threshold to about 85 bpm at breakpoint 1.

Then a portion of the curve of lower slope is encountered in region II, where the heart rate more gradually increases with increasing workload up to breakpoint 2 at about 0.3 g of acceleration, which is consistent with acceleration forces experienced when walking slowly on a level surface (for autocalibration). This region of the curve also provides increases to a rate of about 90 bpm at breakpoint 2 for maximum bicycle exercise.

Region III of the algorithmic curve of FIG. 4 has a steeper slope than region II, reflecting a more rapidly increasing heart rate with increasing workload during walking. For example, the slope of region III approximates a pacing rate increase of 100 ppm per g of acceleration. In region IV, the slope of the curve flattens considerably so that the pacing rate will not increase substantially beyond about 140 ppm, even for an increasing workload.

Region I of the curve has the steepest slope, equal to a pacing rate increase of about 250 ppm/g of acceleration. Region II exhibits an increase in pacing rate versus acceleration of about 50 ppm/g, about the same as region IV. Breakpoint 3 is preferably set at about 0.7 g. Shifting the curve upwardly or downwardly, as indicated by the dotted lines in FIG. 4, provides greater or lesser sensitivity, respectively, of pacing rate to change in acceleration force (and activity signal).

Figure 5:
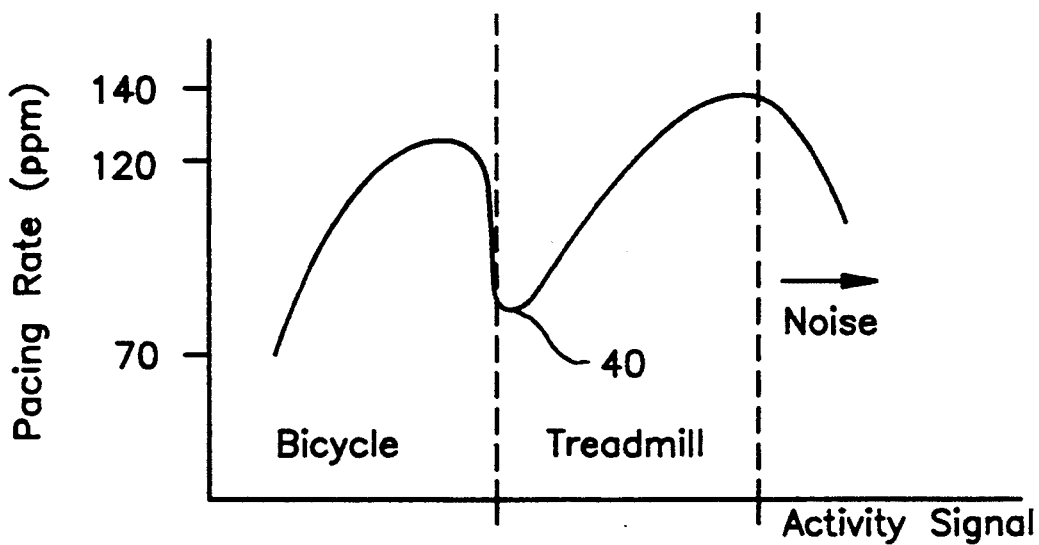
FIG. 5 is yet another alternative algorithmic curve of pacing rate versus exercise involving two different types of exercise for multi-activity sensing and control.

Referring to FIG. 5, in the extreme two rather distinct curves may be developed. The first is a bicycling curve for a pacing rate which rises rapidly with relatively moderate increases in activity signal in a lower amplitude range below the range typically experienced in walking, and which then dips sharply to a transition zone. Thus, the rate drops at a point of slightly increasing workload after an upper rate has been reached, as typically occurs in bicycle exercise. The second curve is a walking curve which rises from the transition zone at a higher level of activity signal but somewhat less sharply than the initial part of the bicycling curve so that the heart rate increases less rapidly commencing at a higher level of accelerational forces than is encountered in bicycle exercise. At a heart rate of about or slightly higher than 140 bpm, the rate drops for increasing workload beyond a predetermined activity signal level, based on an assumption that signals generated above that level are more likely to be noise than the result of true physical activity.

The dual curve of FIG. 5 may alternatively be employed in the activity pacemaker, in place of either a curve selected from the family of FIG. 3 or the curve of FIG. 4, to control the pacing rate relative to the amplitude of the activity signal. In each instance, the activity signal additionally can be derived by passing the components of the output signal of the activity sensor through a low pass filter for better distinguishing true activity signals from noise, as taught for example in the '863 patent. In the FIG. 5 curve, at low magnitudes of accelerational forces and consequently relatively low amplitudes of the activity signal, the pacing rate increases rapidly with slight increases in the workload, consistent with the smooth motion of the legs during bicycling, and placement of the accelerometer in the chest region. In the exemplary curve, the rate goes from about 70 ppm to about 120 ppm before dropping rather sharply with increasing signal amplitude. The low point 40 (i.e., proper lowest rate for the particular patient) of the transition between the bicycle and treadmill curves is determined by autocalibration in which the patient goes through a moderate walking exercise for a period of about three minutes and heart rate is observed. The less rapidly increasing heart rate at the higher levels of amplitude of the activity signal in the treadmill curve is consistent with the pedal impacts during walking, for placement of the accelerometer in the patient's chest region.

Any of the foregoing curves or corresponding algorithms may be used for rate control in the exemplary cardiac pacemaker 50 of FIG. 6. The components of the pulse generator of the pacemaker are housed in a hermetically sealed biocompatible case 52. The term "pulse generator" is used in this respect in the broad sense of the vernacular in the art, as encompassing substantially everything in the pacemaker other than the lead and associated pacing (and/or sensing) electrodes. The overall pulse generator includes a battery 58, a generator 59 having a controllably variable pulse rate for generating the stimulating pulses to be delivered to the patient's heart, processing circuitry 60 for the activity signal(s) from an activity sensor or sensors 53, a programmable nonvolatile semiconductor memory 61 for storing the algorithmic curves and other data for the calculations and comparisons to be performed, together with logic circuitry 62 for use in sampling and comparison and other logic functions including control of the operation of a rate control circuit 64 for pulse generator 59. A crystal controlled timer 65 controls the timing of the logic, rate control and pulse generator.

The activity sensor 53 may be housed within case 52 or as shown in FIG. 6, in a separate sealed case composed of biocompatible material for implantation separate from but electrically connected to the control circuitry of the pulse generator, as shown in FIG. 11, where like components are designated by like reference numbers. Either way, the sensor is mechanically isolated from the case to avoid being affected by direct pressure on the case. The sensor may, for example, comprise an accelerometer of piezoelectric, piezoresistive or piezocapacitive type, to generate an electrical signal having amplitude and frequency components representing accelerational forces on or movements by the patient. A suitable hybrid semiconductor version of an activity sensor is described in the '615 patent. A filter in the processing circuit 60 has a low frequency response characteristic for passing components of the activity sensor output signal. The low-pass signal is further processed in conjunction with the logic and memory circuits to select the proper algorithmic curve or curve portion described above for setting and varying the rate of the pacing pulses generated by generator 59 under the control of rate control circuit 64, according to the type of physical exercise in which the patient is engaged.

The output pulses of pulse generator 59 are applied to a conventional connector 54 on a header of the case 52, which accepts the proximal end of a pacing lead 55 having a stimulating electrode or electrode array 56 at its distal end. The pacing lead is typically an endocardial lead which is inserted through the superior vena cava to position the stimulating electrode in excitable relation to myocardial tissue in the appropriate chamber(s) of the right side of the patient's heart. The pacemaker may be configured for unipolar or bipolar stimulation.

Rather than using the magnitude of accelerational forces as the determinant for selection of the proper curve or curve portion to control the pacing rate, it is possible to make the selection by discriminating between the different types of exercise; that is, by differentiating their individual patterns from one another and recognizing which is which. The mean and the standard deviation of the output activity signal may be calculated and the latter then divided by the former, using the processing, logic and memory circuits of the pulse generator. Large deviations from the mean are discarded as random occurrences, while small deviations are considered for differentiating the different types of exercise or activity of the patient. Below a predetermined level of deviation at either side of the mean, true physical exercise such as walking or bicycling is indicated, whereas the activity outside that level is of a more random and even spasmodic nature. Within the boundaries of the predetermined level of deviation another boundary level exists, above which is indicative of bicycling exercise, and below which is indicative of walking exercise, for example. In any event, different types of regular physical exercise can be discriminated from one another in the most simple form by the calculated level relative to a positive or negative threshold level.

For greater reliability, the sensor output signals are processed to compare the standard deviation and the mean over time, which is ideally suited for low level activity signals. A running average of the comparison is calculated in blocks of time such as one second each over a substantially longer time interval, say, 32 seconds. The 32 blocks in this example are processed on a first in, first out basis. Signal continuity and consistency over even this relatively brief averaging interval serves to rule out minor movements and other perturbations constituting noise.

Calculation of the standard deviation relative to the mean of the signal as the determinant for differentiating between different types of exercise is applicable as well to exercise signals generated or derived from sources other than a pure activity sensor, such as from the exemplary physiological parameter sensors which were mentioned earlier herein (e.g., central venous blood temperature sensors, minute ventilation sensors, blood oxygen saturation sensors, etc.). In the circuit of FIG. 6, sensor 53 might therefore be such a physiologic parameter sensor, and the processing of its output would be accomplished in a manner similar to that outlined above, except that the signal would not be restricted to the low pass band. Here again, large deviations from the mean are discarded, while smaller deviations are treated as statistically normally-occurring signals which may be subjected to further processing and calculations in the process of exercise discrimination.

Such calculations also provide the capability to make comparisons between the pattern or features of a particular exercise signal (again, whether the signal is generated from pure activity such as by detecting movements of the patient or is of physiological origin detected from intrinsic parameters) and a library of stored patterns or features indicative of particular types of exercise, to identify and recognize the type of exercise being performed by the patient. Once such pattern recognition is achieved, the proper algorithmic curve of heart rate versus workload (or other applicable parameter) may be selected as the appropriate response function to control the generation of pacing pulses. For each new activity engaged in and identified through pattern recognition, a new response curve designated for that activity is substituted according to the programming of the device. The curves (algorithms) and the library of patterns are stored in memory unit 61 of pulse generator 50. If pattern recognition is applied to the sensor output, it is understood that low pass filtering is not applied to the activity signal from an accelerometer since one technique for performing pattern recognition applies spectral frequency analysis to the raw signal.

The use of such pattern or template recognition techniques is limited in that not every different type of exercise and associated workload demands a unique pacing rate function. However, bicycling and treadmill exercise exemplify at least two different types of physical exercise for which different rate response curves are applicable. The different activity/different response curve programming of the pacemaker will depend at least in part on the nature of the exercise, the type and location of the sensor in or on the patient's body, and, in the case of a pure activity sensor, e.g., an accelerometer or the like, the extent to which the accelerational forces are transmitted through the anatomy and detected by the sensor.

Referring to FIG. 7, activity sensor 53 may actually include a pair of mercury ball sensors of the type described in U.S. Pat. No. 4,846,195, which is also assigned to the assignee of the present invention and incorporated fully herein by reference. The two sensors 67, 68 are affixed together with an orientation of 90 degrees to one another. By making the relative orientation of the two sensors orthogonal and fixed at all times, the activity signal output of each can be used for discrimination between physical activity types without regard to a change in their absolute orientation.

Preferably, the mercury ball sensors are implanted in a separate case from case 52 of pulse generator 50, oriented such that one (67) is a sagittal sensor (i.e., in a plane parallel to the median plane of the body) and the other (68) is a lateral sensor. In the configuration shown, one sensor is somewhat smaller than and assembled within the other in this fixed orientation, but other assembly techniques and relative sensor sizes may alternatively be employed. The lead for connecting the sensors in their separate case to the overall pulse generator 50 may be of a known multiple contact type. As the patient moves, one or both mercury balls will roll about within their respective chambers and make and break contact with electrodes (electrical contacts) disposed about the chamber. The combined movements of the mercury balls within the two sensors, making and breaking connections between adjacent electrodes (closures and openings with time) may be detected to provide information regarding the physical position of the patient.

Figure 8:
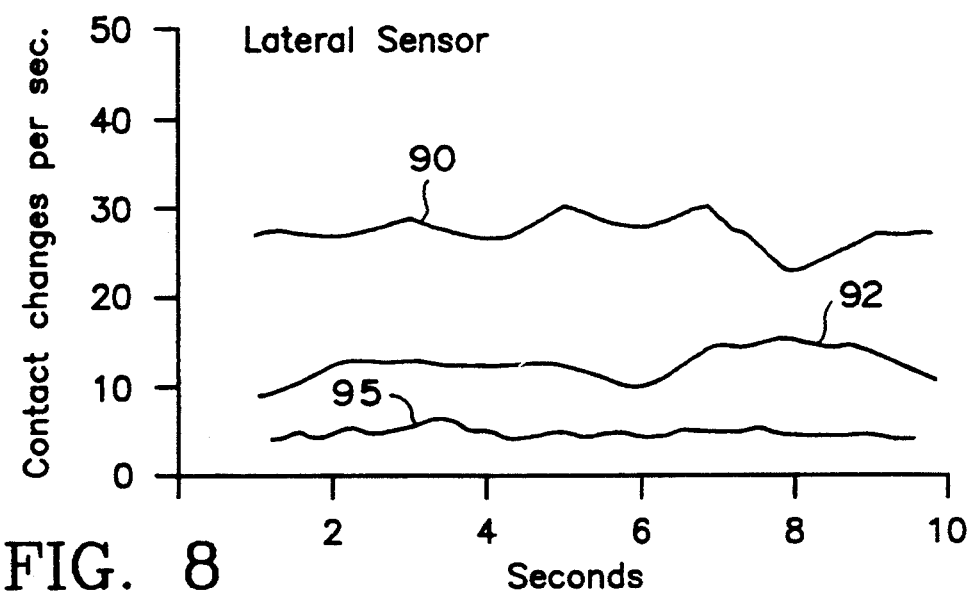
FIG. 8 is a graph of differing activity types for number of contact changes per second over a block of time, using a mercury ball sensor to detect activity.

When the patient is walking or bicycling, the output of each sensor is relatively smooth (although one will produce a signal of greater magnitude than the other as is evident from the charts of FIGS. 1A and 1B), as indicated in FIG. 8. Curve 90 represents number of contact changes per second in the lateral mercury ball sensor (ordinate) relative to elapsed time in seconds (abscissa) for a subject walking at a rate of 4.8 kilometers per hour (km/h) on a+10 percent grade. Curve 92 is the same for the subject walking at 3.2 km/h at 0% grade. Curve 95 illustrates the same for the subject riding a stationary bicycle, and shows that the number of contact changes per second in the lateral mercury ball sensor for this activity is considerably less than for either of the walking activities. The activity signals from the sensors are processed in the processing, memory and logic circuitry of pulse generator 50 with identification of each contact of each sensor, the number of contact closures and openings for each contact, and the instant of time at which each closure or opening took place within a specified time interval. A multiple contact lead connector of the type disclosed in U.S. Pat. No. 4,971,057 is may be used between the sensors and the pulse generator to facilitate this processing.

Figure 9:
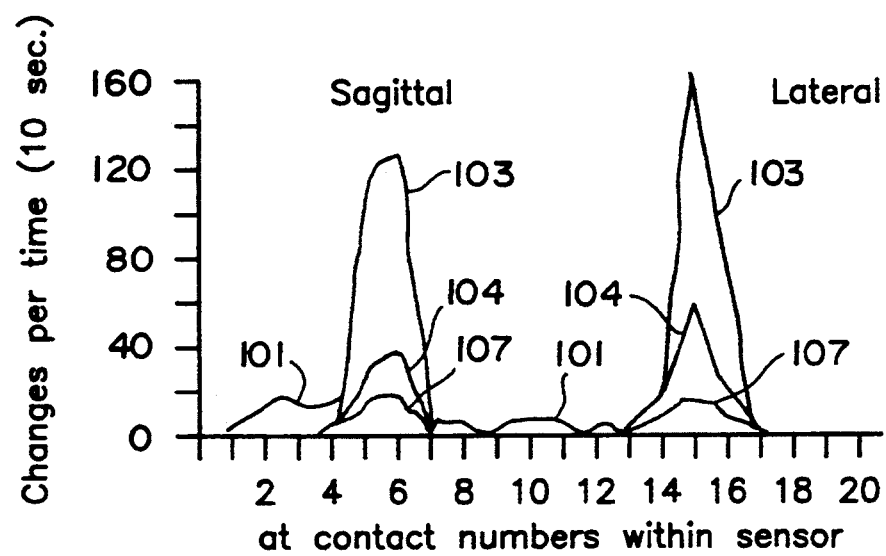
FIG. 9 is a graph of sensor contact changes with time relative to numbered contacts for different types of exercise by the patient, using the mercury ball sensors of FIG. 7.

In an experiment conducted with a healthy volunteer subject, graphically charted in FIG. 9, the number of contact changes with time (ten second intervals) for each of the sagittal sensor and lateral sensor worn by the subject were plotted on the Y-axis against the designated numbered contacts of each sensor on the X-axis for various activities. The activities included random movement consisting of slight changes of physical position (designated by curve 101), walking on a treadmill at 4.8 km/h with a+10% grade (curve 103), walking on a level treadmill at 3.2 km/h (curve 104), and bicycling on a stationary cycling machine at workloads comparable to those for the treadmill exercises (curve 107). These are the same events as are charted in FIG. 8, described above.

Figure 10:
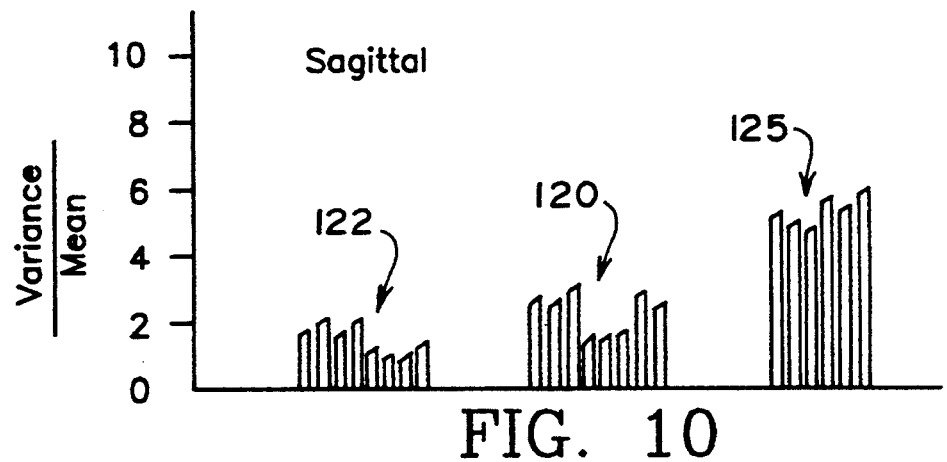
FIG. 10 is a plot of the quotient of the standard deviation relative to the mean of an activity signal, calculated from the contact changes over time in a mercury ball sensor for several different types of physical activity.

FIG. 10 is a plot for the sagittal sensor, of the quotient of the standard deviation divided by the mean of the output signal of such a sensor (here also, in the frequency band below 10 Hz or less) for some of these exercise types. The plot demonstrates the capability of this calculation to differentiate between different types of physical exercise and recognize a specific type through its patterns or features. An analogous showing was observed for the lateral sensor, which is not illustrated here. For the 3.2 km/h treadmill exercise the discrete calculations (designated by reference number 120) were somewhat varied but produced consistently higher values than the otherwise similar results obtained for the 4.8 km/h walking exercise (122). Similarly, the stationary bicycling exercise (125) produced consistently higher values than those obtained from the 3.2 km/h treadmill exercise (120). Each activity is distinguishable from the others by resort, for example, to an average of the calculated values over time relative to a respective preselected threshold value.

Thus, the invention, in its various aspects and features, provides implantable programmable rate responsive cardiac pacemakers which are capable of recognizing and responding differently to at least some of the multiple types of exercise in which the patient may engage. Although certain preferred embodiments and methods have been disclosed herein, it will be apparent from the foregoing disclosure to those skilled in the art that variations and modifications of such embodiments and methods may be made without departing from the true spirit and scope of the invention. Accordingly, it is intended that the invention shall be limited only to the extent required by the appended claims and the rules and principles of applicable law.

What is claimed is:

1. A variable rate cardiac pacemaker adapted and configured to be implanted in a human patient, and adaptive in rate to different types of patient exercise such as walking and bicycling, comprising:

sensor means adapted to respond to physical exercise by the patient for producing an electrical signal representative of the specific type of physical exercise being engaged in by the patient, pulse generator means for controllably generating pacing pulses in a range of rates adapted to stimulate the patient's heart, memory means for storing different algorithms denoting heart rate as a function of respective ones of the different types of exercise for a healthy person with a normally functioning cardiovascular system, and control means responsive to signals produced by said sensor means representative of different types of exercise engaged in by the patient for discriminating between specific types of exercise represented by the respective signals produced by said sensor means, including means having access to said different algorithms of said memory means and responsive to the type of exercise determined by the discrimination for selecting the algorithm corresponding to the type of exercise being engaged in by the patient, and including means to control the pacing rate of said pulse generating means according to the selected algorithm.

2. The invention of claim 1, wherein:
said control means includes means for examining the magnitude of the signal produced by the sensor means over time to distinguish different types of physical exercise from one another.

3. The cardiac pacemaker of claim 1, wherein:
said control means includes means for determining standard deviation and mean of the respective signal produced by the sensor means, and for calculating quotient of standard deviation divided by mean to distinguish different types of physical exercise from one another.

4. The cardiac pacemaker of claim 3, wherein:
said means for calculating quotient of the standard deviation divided by the mean of the signal produced by the sensor means comprises timing means for defining prescribed intervals of time over which the calculation is to be performed, and means for performing the calculation over said prescribed intervals of time.

5. The invention of claim 1, wherein:
said control means includes means for comparing the patterns of signals produced by the sensor means over time to distinguish different types of physical exercise from one another.

6. The invention of claim 5, wherein:
the means for comparing the patterns of signals produced by the sensor means over time compares each pattern with those among a library of patterns of exercise representative signals produced by a sensor corresponding to said sensor means, and
said control means further includes means for storing said library of patterns to make them available for comparison with patterns of signals produced by the sensor means.

7. The invention of claim 1, wherein:
said control means includes means for recognizing patterns of signals produced by the sensor means by performing spectral analysis of the signals to distinguish different types of physical exercise from one another.

8. The cardiac pacemaker of claim 1, wherein:
said sensor means is an activity sensor adapted to respond to the patient's movements.

9. The cardiac pacemaker of claim 8, wherein:
said activity sensor is an accelerometer for detecting accelerations attributable to physical exercise by the patient.

10. The cardiac pacemaker of claim 9, further including:
a case housing said pulse generator means: and
means for mechanically isolating said accelerometer from said case to render the accelerometer substantially unresponsive to pressure on the case.

11. The cardiac pacemaker of claim 9, further including:
a case housing said pulse generator means; and
a second case housing said accelerometer for implantation in the patient separate from the first named case.

12. The cardiac pacemaker of claim 9, wherein:
said accelerometer comprises integrated electronic circuit means responsive to three-dimensional movement thereof for producing said electrical signal.

13. The cardiac pacemaker of claim 12, wherein:
said integrated electronic circuit means is a silicon based mechanoelectrical converter.

14. The cardiac pacemaker of claim 13, wherein:
said mechanoelectrical converter is selected from the group consisting of piezoelectric, piezocapacitive and piezoresistive converters to convert patient movement to said electrical signal representative thereof.

15. The cardiac pacemaker of claim 8, wherein:
said control means includes means for processing the signal produced by said activity sensor through a low pass filter having a frequency pass band below 10 Hz, to restrict the processed signal to components indicative of exercise by the patient.

16. The cardiac pacemaker of claim 1, wherein:
said sensor means comprises
first and second mercury ball activity sensors each having a multiplicity of contacts in a planar array about which the mercury ball may roll for intermittently establishing electrical connections with the contacts of the respective array upon physical movement of the patient, said sensors fixed with the respective arrays in orthogonal orientation to one another,
said control means comprising means responsive to closures and openings of each array of contacts as the respective mercury ball makes and breaks electrical connections therewith for calculating the quotient of the standard deviation, as variations, divided by the mean value, over time, of electrical closures and openings of each array of contacts resulting from the making and breaking of electrical connections by the respective mercury ball, and comparison means for comparing said quotient to a predetermined value to distinguish the different types of physical exercise by the patient.

17. In combination with an implantable rate responsive pacemaker having a pulse generator adapted to generate pulses for stimulating a patient's heart at a variable pacing rate in response to a control signal derived from activity sensing means carried by the patient, the improvement comprising:

control means adapted to respond to each of a plurality of distinct and different activity signals generated by said activity sensing means representing different types of physical activity of the patient, as said control signal, for processing said control signal to detect the specific type of activity being engaged in by the patient and to adjust the pacing rate according to that specific type of activity, said control means including means for storing a plurality of different representations of heart rate as a function of acceleration signals arising from the respective types of physical activity for a healthy person with a normally functioning cardiovascular system, and means for continuously and automatically selecting a particular one of said representations according to the specific type of physical activity detected by said control means from which to adjust the pacing rate.

18. The improvement of claim 17, wherein:
said control means further includes means responsive to said control signal for deriving a pattern therefrom characteristic of the specific type of physical activity represented by said control signal, and means for comparing said pattern to a library of stored patterns characteristic of distinct and different types of physical activity from which to detect the specific type of physical activity represented by said control signal.

19. The improvement of claim 18, wherein:
the pattern deriving means includes means for calculating the standard variation of the control signal relative to the mean of the control signal over time.

20. The improvement of claim 18, wherein:
the pattern deriving means includes means for performing a spectral analysis of the control signal.

21. A method of distinguishing distinct and different types of physical activity, such as walking and bicycling engaged in by a patient, from one another for the purpose of controlling the pacing rate of a variable rate pacemaker carried by the patient according to the specific type of physical activity in which the patient is engaged, which comprises:
detecting one of an extrinsic parameter and an intrinsic parameter having a variable value representing activity of the patient,
generating a control signal indicative of instantaneous value of said parameter,
processing the control signal over time to derive therefrom the nature of the physical activity being engaged in by the patient, and
controlling the pacing rate of the pacemaker according to the distinguished specific type of activity.

22. The method of claim 21, wherein the step of processing the control signal includes:
calculating the mean value of the control signal variances of the control signal, and the quotient of the variances divided by the mean value of the control signal over time to uniquely distinguish the specific type of activity in which the patient is engaged from others of the distinct and different activity types.

23. The method of claim 21, wherein the step of processing the control signal includes:
comparing the characteristic pattern of the control signal against characteristic patterns associated with each of the distinct and different activity types, to substantially uniquely distinguish the specific type of activity in which the patient is engaged from others of the distinct and different activity types.

24. A method for discriminating true and consistent physiological signals such as a patient's sinus rhythm having a variable value depending on patient exercise, from inconsistent or noise signals such as intermittent or otherwise faulty sensing, to control the pacing rate of a variable rate pacemaker carried by the patient in response to the variable value of the physiological signals, which comprises the steps of:
sensing a physiological parameter having a variable value representing the extent of exercise engaged in by the patient,
converting the sensed parameter to an output signal indicative of instantaneous value of said parameter and any noise components present thereon,
processing the output signal by calculating variances, as the standard deviation, and the mean value of the output signal, and calculating the standard deviation relative to the mean value of the output signal over time to discriminate the true variations of the value of the physiological parameter from noise components of the output signal, and
controlling the pacing rate of the pacemaker in response to the processed output signal to vary the pacing rate according to true variations of the value of the physiological parameter while suppressing any contribution attributable to noise components, and thereby, according to true patient exercise.

25. Apparatus for discriminating true and consistent physiological signals such as a patient's sinus rhythm having a variable value depending on patient exercise, from inconsistent or noise signals such as intermittent or otherwise faulty sensing, to control the pacing rate of a variable rate pacemaker carried by the patient in response to the variable value of the physiological signals, comprising:
sensor means for sensing a physiological parameter having a variable value representing the extent of exercise engaged in by the patient,
converting means responsive to the sensed parameter for converting the sensed parameter to an output signal indicative of instantaneous value of said parameter and any noise components present thereon,
processing means responsive to the output signal for processing the output signal by calculating variances, as the standard deviation, and the mean value of the output signal, and calculating the standard deviation relative to the mean of the output signal over time to discriminate the true variations of the value of the physiological parameter from noise components of the output signal, and
control means for controlling the pacing rate of the pacemaker in response to the processed output signal to vary the pacing rate according to true variations of the value of the physiological parameter while suppressing any contribution attributable to noise components.

26. A cardiac pacemaker adapted to be carried by a patient and to generate an adjustable pacing rate that recognizes the type and tracks the strenuousness of activity of the patient, comprising:
sensor means responsive to activity of the patient for producing an output representative thereof and including, as well, components attributable to sensed sources other than pure activity that tend to obscure the type and strenuousness of the activity;

control means responsive to the sensor means output for developing a control signal representative of patient activity to adjust the pacing rate based on pure activity of the patient, including means for suppressing a contribution to pacing rate of said components attributable to sources other than pure activity according to the standard deviation relative to the mean of the output, and generator means responsive to said control signal for generating pulses at an adjustable pacing rate having an instantaneous value based on said pure activity of the patient.

27. The cardiac pacemaker of claim 26, wherein:

said control means includes means responsive to the output of said sensor means for calculating the standard deviation and the mean value of said output, and for dividing the standard deviation by the mean value of the sensor means output over time to discriminate the pure activity component thereof from said components attributable to sources other than pure activity.

28. The cardiac pacemaker of claim 27, wherein:

said control means further includes recognition means responsive to calculation of quotient of the standard deviation relative to the mean value of the sensor means output over time for recognition of the type of physical activity being engaged in by the patient, and means responsive to said recognition and coupled to said generator means for adjusting the pacing rate of the pulses generated by said generating means according to the recognized type of physical activity.

29. The cardiac pacemaker of claim 28, wherein:

said sensor means comprises an accelerometer.

30. A method of adjusting the pacing rate of a cardiac pacemaker to be carried by a patient, according to the type and strenuousness of activity of the patient, including the steps of:

sensing physical activity of the patient to produce an output representative of said physical activity, and including in said output, as well, components attributable to sensed sources other than pure physical activity that tend to obscure the type and strenuousness of the physical activity;

generating pulses at an adjustable rate to set the heart rate of the patient, and adjusting the pacing rate based on the output component attributable to sensed pure activity of the patient and type of such activity to suppress a contribution to pacing rate of said components attributable to sources other than pure physical activity, by calculating the standard deviation and mean value of said output and dividing standard deviation by mean value over time.

* * * * *